United States Patent [19]
Hillman et al.

[11] Patent Number: 5,837,493
[45] Date of Patent: Nov. 17, 1998

[54] HUMAN GALECTINS

[75] Inventors: Jennifer L. Hillman, San Jose; Surya K. Goli, Sunnyvale; Olga Bandman; Phillip R. Hawkins, both of Mountain View; Joanne R. Petithory, Fremont, all of Calif.

[73] Assignee: Incyte Pharmaceuticals, Inc., Palo Alto, Calif.

[21] Appl. No.: 788,584

[22] Filed: Jan. 23, 1997

[51] Int. Cl.$^6$ .............................. C12N 15/00; C12N 1/20; C12P 21/02; C07H 21/04

[52] U.S. Cl. .................. 435/69.1; 439/172.3; 439/320.1; 439/252.3; 439/325; 439/348; 439/371; 536/23.1; 536/23.5

[58] Field of Search ................................ 435/320.1, 69.1, 435/172.3, 252.3, 325, 348, 371; 536/23.1, 23.5

[56] References Cited

PUBLICATIONS

Tureci, Ö, et al., "H. Sapiens mRNA for galectin," *Database EMBL—EMHUM2*, Entry HSZ49107, Acc. No. Z49107, Dec. 6, 1995.

Tureci, Ö, et al. "Molecular definition of a novel human galectin which is immunogenic in patients with Hodgkin's disease," *J. Biol. Chem.*, vol. 272, No. 10, pp. 6416–6422, XP002065487, Mar. 7, 1997.

Takeda, J., "*EST similar to Hodgkin Disease associated lectin,*" XP002065490 Database EMBL, EMEST10, Entry HSC4706, Acc. No. C06470, Aug. 25, 1996.

Barondes, S.H. et al., "Structure and Function of a Large Family of Animal Lectins" *J.Biol.Chem.* (1994) 269:20807–20810.

Stoolman, L.M., "Adhesion Molecules Controlling Lymphocyte Migration", *Cell* (1989) 56:907–910.

Abbott, W.M. et al., "Soluble 14–kDa β–Galactoside–specific Bovine Lectin", *J.Biol Chem.* (1991) 266:5552–5557.

Hirabayashi, J. et al., "Effect of Amino Acid Substitution by Site–directed Mutagenesis on the Carbohydrate Recognition and Stability of Human 14–kDa β–Galactoside–binding Lectin", *J.Biol.Chem.* (1991) 35:23648–23653.

Do, K. et al., "Lamp–1 in CHO Cells is a Primary Carrier of Ply–N–acetyllactosamine Chains and is Bound Preferentially by a Mammalian S–Type Lectin", *Biochem.Biophys. Res.Commun.* (1990) 173:1123–1128.

Skrincosky, D.M. et al., "Galaptin–mediated Adhesion of Human Ovarian Carcinoma A121 Cells and Detection of Cellular Galaptin–binding Glycoproteins", *Cancer Res.* (1993) 53:2667–2675.

Erratum (1993) *Cancer Res.* (1993) 53:3652.

Gu, M. et al., "Selective modulation of the interaction of $\alpha_7\beta_1$ integrin with fibronectin and laminin by L–14 lectin during skeletal muscle differentiation", *J.Cell Sci.* (1994) 107:175–181.

Mahanthappa, N.K. et al., "Rat olfactory neurons can utilize the endogenous lectin, L–14 in a novel adhesion mechanism", *Development* (1994) 120:1373–1384.

Liu, F., "S–type mammalian lectins in allergic inflammation", *Immunol.Today* (1993) 14:486–490.

Frigeri, L.G. et al., "εBP, a β–Galactoside–Binding Animal Lectin, Recognises IgE Receptor (FcεRI) and activates Mast Cells", *Biochem.* (1993) 32:7644–7649.

Oda, Y. et al., "Soluble Lactose–binding Lectin from Rat Intestine with Two Different Carbohydrate–binding Domains in the Same Peptide Chain", *J.Biol.Chem.* (1993) 268:5929–5939.

Gitt, M.A. et al., "Sequence and Mapping of Galectin–t, a β–Galactoside–binding Lectin, Found in Rat Erythrocytes", *J.Biol. Chem.* (1995) 270 (10)5032–5038. (GI 727176).

Magnaldo, T. et al., "Galectin–7, a Human 14–kDa S–Lectin, Specifically Expressed in Keratinocytes and Sensitive to Retinoic Acid", *Develop.Biol.* (1995) 168:259–271.

Madsen, P. et al., "Cloning, Expression, and Chromosome Mapping of Human Galectin–7", *J.Biol.Chem.* (1995) 270:5823–5829.

Hadari, Y.R., et al., "Galectin–8", *J.Biol.Chem.* (1995) 270:3447–3453.

Raz, A. et al., "Endogenous galactoside–binding lectins:a new class of functional tumor cell surface molecules related to metastasis", *Cancer Metastasis Rev.* (1987) 6:433–452.

Jackson, R.J. et al., "Do the poly(A) tail and 3' untranslated region control mRNA translation?", *Cell* (1990) 62:15–24.

Raz, A. et al., "Differential Expression of Endogenous Lectins on the Surface of Nontumorigenic, tumorigenic, and Metastatic Cells", *Cancer Res.* (1986) 46:3667–3672.

Raz, A. et al., "Evidence for the Role of 34–kDa Galactoside–Binding Lectin in Transformation and Metastasis", *Int.J.Cancer* (1990) 46:871–877.

Cerra, R.F. et al., "Three soluble rat beta–galactoside–binding lectins." *J.Biol.Chem.* (1985) 260:10474–10477.

Sahin, U. (Direct Submission), GenBank Suquence Database (Accession Z49107), National Center for Biotechnology Information, National Library of Medicine, Bethesda, Maryland, 20894 Feb. 21, 1996.

Database GenBank, Subsection EST Accession No. T89534, Wash U—Merck EST Project, Mar. 20, 1995.

*Primary Examiner*—Lila Feisee
*Assistant Examiner*—Lin Sun-Hoffman
*Attorney, Agent, or Firm*—Lucy J. Billings; Incyte Pharmaceuticals, Inc.

[57] ABSTRACT

The present invention provides two novel human galectins (designated individually as GAL-5HA and GAL-5HB, and collectively as GAL-5H) and polynucleotides which identify and encode GAL-5H. The invention also provides genetically engineered expression vectors and host cells comprising the nucleic acid sequences encoding GAL-5H and a method for producing GAL-5H. The invention also provides for use of GAL-5H and agonists, antibodies, or antagonists specifically binding GAL-5H, in the prevention and treatment of diseases associated with expression of GAL-5H. Additionally, the invention provides for the use of antisense molecules to polynucleotides encoding GAL-5H for the treatment of diseases associated with the expression of GAL-5H. The invention also provides diagnostic assays which utilize the polynucleotide, or fragments or the complement thereof, and antibodies specifically binding GAL-5H.

9 Claims, 7 Drawing Sheets

```
              9              18              27              36              45             54
5'   C TCT ACA ANG GAC TTC CTA GTG GGT GTG AAT GGC AGC GGT GGC CAC AGN GGC 63              72              81              90              99            108
    GGC GGN GAG ATG GCC TTN AGC GGT TCC CAG GCT CCC TAC CTG AGT CCA NCT GTC
             M   A   X   S   G   S   Q   A   P   Y   L   S   P   X   V 117             126             135             144             153            162
    CCC TTT TCT GGG ACT NTT CAA GGA GGG CTG TAC CCA TCC AAG TCC ATC CTC CTG
     P   F   S   G   T   X   Q   G   G   L   Y   P   S   K   S   I   L   L 171             180             189             198             207            216
    TCA GGC ACT GTC CTG CCC AGT GCT CAG AGG TTC CAC ATC AAC CTG TGC TCT GGG
     S   G   T   V   L   P   S   A   Q   R   F   H   I   N   L   C   S   G 225             234             243             252             261            270
    AAC CAC ATC GGC TTY CAC CTG AAC CCC CGT TTT GAT GAG AAT GCT GTG GTC CGC
     N   H   I   G   F   H   L   N   P   R   F   D   E   N   A   V   V   R 279             288             297             306             315            324
    AAC AAC CAG ATC GAC AAC TYC TGG GGG TCT GAG GAG CGA AGT CTG CCC CGA AAA
     N   N   Q   I   D   N   X   W   G   S   E   E   R   S   L   P   R   K 333             342             351             360             369            378
    ATG CCC TTC GTC CGT GGC CAG AGC TTC TCA GTG TGG ATC TTG TGT GAA GCT CAC
     M   P   F   V   R   G   Q   S   F   S   V   W   I   L   C   E   A   H 387             396             405             414             423            432
    TGC CTC AAG GTG GCC GTG GAT GGT CAG CAC CTG TTT GAA TAC TAC CAT CGC CTG
     C   L   K   V   A   V   D   G   Q   H   L   F   E   Y   Y   H   R   L 441             450             459             468             477            486
    AGG AAC CTG CCC ACC ATC AAC AGA CTG GAA GTG GGG GGN GAC ATC CAG CTG ACC
     R   N   L   P   T   I   N   R   L   E   V   G   G   D   I   Q   L   T 495             504             513             522             531            540
    CAT GTG CAG ACA TAG GCG GCT TCC TGG GCC TGG GGC CGG GGG TNG GGT GTG GGG
     H   V   Q   T 549             558
    CAG TCT TGG TCT TCA TAA AC 3'
```

FIGURE 1

```
                 9              18              27              36              45              54
5' GAA CGG GAT CCT CTT CGT GCA GTA CTT CCA CCG CGT GCC CTT CCA CCG TGT GGA 63              72              81              90              99             108
   CAC CAT CTC CGT CAA TGG CTC TGT GCA GCT GCC AAC CCG GCT CCC ATT ACC CAG 117             126             135             144             153             162
   ACA GTC ATC CAC ACA GTG CAG AGC GCC CCT GGA CAG ATG TTC TCT ACT NCC GGC
                                                         M   F   S   T   X   G 171             180             189             198             207             216
   ATC CCA CCT ATG ATG TAC CCC CAC CCC GGC TAT CCG ATG CCT TTC ATC ACC ACC
   I   P   P   M   M   Y   P   H   P   G   Y   P   M   P   F   I   T   T 225             234             243             252             261             270
   ATT CTG GGA GGG CTG TAC CCA TCC AAG TCC ATC CTC CTG TCA GGC ACT GTC CTG
   I   L   G   G   L   Y   P   S   K   S   I   L   L   S   G   T   V   L 279             288             297             306             315             324
   CCC AGT GCT CAG AGG TTC CAC ATC AAC CTG TGC TCT GGG AAC CAC ATC GCC TTC
   P   S   A   Q   R   F   H   I   N   L   C   S   G   N   H   I   A   F 333             342             351             360             369             378
   CAC CTG AAC CCC CGT TTT GAT GAG AAT GCT GTG GTC CGC AAC ACC CAG ATC GAC
   H   L   N   P   R   F   D   E   N   A   V   V   R   N   T   Q   I   D 387             396             405             414             423             432
   AAC TTC TGG GGG TCT GAG GAG CGA AGT CTG CCC CGA AAA ATG CCC TTC GTC CGT
   N   F   W   G   S   E   E   R   S   L   P   R   K   M   P   F   V   R 441             450             459             468             477             486
   GGC CAG AGC TTC TCA GTG TGG ATC TTG TGT GAA GCT CAC TGC CTC AAG GTG GCC
   G   Q   S   F   S   V   W   I   L   C   E   A   H   C   L   K   V   A 495             504             513             522             531             540
   GTG GAT GGT CAG CAC CTG TTT GAA TAC TAC CAT CGC CTG AGG AAC CTG CCC ACC
   V   D   G   Q   H   L   F   E   Y   Y   H   R   L   R   N   L   P   T 549             558             567             576             585             594
   ATC AAC AGA CTG GAA GTG GGG GGC GAC ATC CAG CTG ACC CAT GTG CAG ACA TAG
   I   N   R   L   E   V   G   G   D   I   Q   L   T   H   V   Q   T 603             612             621             630             639             648
   GCG GCT TCC TGG CCC TGG GGC CGG GGG CTG GGG TGT GGG GCA GTC TGG GTC CTC 657             666             675             684             693             702
   TCA TCA TCC CCA CTT CCC AGG CCC AGC CTT TCC AAC CCT GCC TGG GAT CTG GGC 711             720             729             738             747             756
   TTT AAT GCA GAG GCC ATG TCC TTG TCT GGT CCT GCT TCT GGC TAC AGC CAC CCT
```

FIGURE 2A

```
              765           774           783           792           801          810
    GGA ACG GAG AAG GCA GCT GAC GGG GAT TGC CTT CCT CAG CCG CAG CAG CAC CTG 819           828           837           846           855          864
    GGG CTC CAG CTG CTG GAA TCC TAC CAT CCC AGG AGG CAG GCA CAG CCA GGG AGA 873           882           891           900           909          918
    GGG GAG GAG TGG GCA GTG AAG ATG AAG CCC CAT GCT CAG TCC CCT CCC ATC CCC 927           936           945           954           963          972
    CAC GCA GCT CCA CCC CAG TCC CAA GCC ACC AGC TGT CTG CTC CTG GTG GGA GGT 981           990           999          1008          1017         1026
    GGC CTC CTC AGC CCC TCC TCT CTG ACC TTT AAC CTC ACT CTC ACC TTG CAC CGT 1035          1044          1053          1062          1071         1080
    GCA CCA ACC CTT CAC CCC TCC TGG AAA GCA GGC CTG ATG GCT TCC CAC TGG CCT 1089          1098          1107          1116          1125         1134
    CCA CCA CCT GAC CAG AGT GTT CTC TTC AGA GGA CTG GCT CCT TTC CCA GTG TCC 1143          1152          1161
    TTA AAA TAA AGA AAT GAA AAT GCT TGT TGG CAC   3'
```

HUMAN GALECTINS

FIELD OF THE INVENTION

This invention relates to nucleic acid and amino acid sequences of novel human galectins and to the use of these sequences in the diagnosis, prevention, and treatment of aberrant hematopoiesis, inflammation, autoimmune disease, and cancer.

BACKGROUND OF THE INVENTION

Lectins are proteins which are defined by their ability to bind carbohydrates specifically and to agglutinate cells. Lectins have been shown to be involved in a wide variety of cellular functions including cell-cell and cell-matrix interactions. Lectins are widespread among plants, invertebrates and mammals.

Animal lectins have been grouped into four distinct families: 1) C-type lectins, which include selecting; 2) P-type lectins; 3) galectins (formerly termed S-type lectins or S-Lac lectins); and 4) pentraxins (Barondes, S. H. et al. (1994) J. Biol. Chem. 269:20807–10). The C-type lectins bind carbohydrate ligands in a $Ca^{2+}$-dependent manner and are structurally related to the asialoglycoprotein receptor. Selectins, a subcategory of the C-type lectins, are composite transmembrane molecules which are involved in cell-cell interactions. The selectins include lymphocyte homing receptors and platelet/endothelial cell surface receptors (Stoolman, L. M. (1989) Cell 56:907–10).

Galectins bind specifically to β-galactoside residues in a thiol-dependent manner. To date, eight galectin types have been identified (galectin-1 through galectin-8). In addition to their affinity for β-galactoside sugars, members of the galectin family share significant sequence similarity in the carbohydrate recognition domain (CRD; also referred to as the carbohydrate-binding domain). In most mammalian galectins, the CRD is encoded by 3 exons, and the majority of the residues conserved between galectins are encoded by the middle one of these three exons. Typically this region contains four β-strands and intervening loops (these β-strands are termed S3, S4, S5, and S6a/S6b according to Barondes et al., supra). Conserved residues or motifs located within the CRDs of mammalian galectins include $H_{45}$, $N_{47}$, $P48$, $R_{49}$, $V_{56}$, $N_{58}$, $W_{65}$, $E_{68}$, $F_{76}$ and $G_{79}$ (numbering according to amino acid sequence of galectin-2 as shown in Barondes et al., supra). The importance of some of these conserved residues for binding carbohydrates has been confirmed by site-directed mutagenesis (Abbott, W. M. and Feizi, T. (1991) J. Biol. Chem. 266:5552–57; Hirabayashi, J. and Kasai, K. (1991) J. Biol. Chem. 266:23648–53). All mammalian galectins which have been analyzed in detail recognize the same structural determinant on lactose (primarily the galactose residue, although there is significant interaction with the glucose residue) and related β-galactosides. In addition to binding β-galactoside sugars, galectins possess hemagglutination activity.

Despite the fact that the cellular milieu contains a large number of β-galactoside-containing glycoconjugates, few naturally occurring glycoconjugates have been shown to bind to specific galectins in vitro, suggesting that interactions between galectins and glycoconjugates are physiologically significant (i.e., galectins do not bind promiscuously to all naturally-occurring glycoconjugates). Laminin, a naturally occurring glycoprotein containing numerous polylactosamine chains, has been shown to be a natural ligand for galectin-1; galectin-3 has also been shown to bind laminin. Laminin is a component of the basal laminate, the extracellular matrix which underlies all epithelia and surrounds individual muscle, fat and Schwann cells. Interaction between cells and the basal laminate is known to influence the migration and/or differentiation of various cell types during mammalian development. Galectin-1 (also known as galaptin, L-14, L-14-I and BHL) is also known to bind to the polylactosamine-rich lysosome-associated membrane proteins (LAMPs) which can be found on the cell surface (Do, K. Y. et al. (1990) Biochem. Biophys. Res. Commun. 173:1123–28; Skrincosky, D. M. et al. (1993) Cancer Res. 53:2667–75; Erratum (1993) Cancer Res. 53:3652), integrin $α_7$, $β_1$, present on skeletal muscle (Gu, M. et al. (1994) J. Cell. Sci 107:175–81) and a lactosamine-containing glycolipid present on olfactory neurons (Mahanthappa, N. K. et al. (1994) Development (Camb.) 120:1373–84). Galectin-3 (also known as Mac-2, EPB, CBP-35, CBP-30 and L-29) has been shown to interact with immunoglobulin E (IgE) and the IgE receptor (Liu, F. T. (1993) Immunol. Today 14:486–90; Frigeri, L. G. et al. (1993) Biochem. 32:7644–49, respectively).

Galectin-1 and -2 exist as homodimers composed of subunits of approximately 130 amino acids (~14 kDa); each subunit forms one compact globular domain which possesses carbohydrate binding activity (i.e., the CRD; Barondes et al., supra). Galectin-3 has one CRD, a short N-terminal domain and an intervening proline, glycine and tyrosine-rich domain which consists of repeats of 7–10 conserved amino acids. These tandem repeats are characteristic of the collagen gene superfamily. The number of repeats varies between mammalian galectin-3 molecules and accounts for the differences in size between galectin-3 from different species of mammals. The N-terminal half of galectin-3 permits the molecule to undergo multimerization upon binding to surfaces containing glycoconjugate ligands. Galectin-4 exists as a monomer of about 36 kDa and has two CRDs connected by a link region that is homologous to the repeating domain of galectin-3 (Oda, Y. et al. (1993) J. Biol. Chem. 268:5929–39). Rat galectin-5 contains a single CRD in a structure similar to galectin-1 and 2; however, galectin-5 exists as a 17 kDa monomer under non-denaturing conditions (Gitt, M. A. et al. (1995) J. Biol. Chem. 270:5032–5038). Despite its monomeric form and monovalency, galectin-5 acts as a weak erythrocyte agglutinin. Since galectin-5 only contains a short N-terminal domain in addition to the CRD, Gitt, et al. (supra) suggest that galectin-5-induced agglutination may occur by protein-protein interactions different than those of the monomeric galectin-3. Human galectin-7 exists as a monomer of approximately 14 kDa (Magnaldo, T. et al. (1995) Develop. Biol. 168:259–71; Madsen, P. et al. (1995) J. Biol. Chem. 270:5823–29). Rat galectin-8 is a monomer of approximately 35 kDa and like galectin-4, has two CRDs in the same polypeptide chain joined by a short (~30 amino acids) link region (Hadari, Y. R. et al. (1995) J. Biol. Chem. 270:3447–53). The link region of rat galectin-8 is not similar to either the link region of galectin-4 or to the proline, glycine and tyrosine-rich repeat domain of galectin-3.

Galectins are expressed in a wide variety of tissues in mammals. Galectin-1 is expressed abundantly in muscle (skeletal, smooth and cardiac), neurons (both motor and sensory), thymus, kidney and placenta. Galectin-2 is expressed in hepatomas. Galectin-3 is expressed most highly in activated macrophages, basophils and mast cells and is also expressed in intestinal and kidney epithelial cells, vascular smooth muscle cells and in some sensory neurons. The expression of galectin-3 has been shown to be elevated in tumors (Raz, A. and Lotan, R. (1987) Cancer Metastasis Rev. 6:433). Rat galectin-4 is expressed in intestinal epithelium and the stomach (a galectin-4 homolog has been isolated from nematodes). Rat galectin-5 is expressed primarily in red blood cells (Gitt et al., supra). Unlike other galectin cDNAs, the rat galectin-5 cDNA contains a long 400 nucleotide 3' untranslated region which may play a role in translational regulation (Jackson, R. J. and Standart, N. (1990) Cell 62:15–24). Human galectin-7 is expressed in keratinocytes and its expression is markedly downregulated in SV40 transformed keratinocytes and in malignant keratinocyte cell lines (Madsen et al., supra; Magnaldo et al., supra). Rat galectin-8 is most highly expressed in lung with significant expression in liver, muscle (cardiac and skeletal) and spleen; low levels of galectin-8 are found in rat brain; expression of rat galectin-8 appears to be developmentally regulated as rat galectin-8 mRNA is expressed at very low levels in whole embryos while high levels of expression are found in adult rat tissues (Hadari et al., supra).

Some galectins have been shown to be secreted (e.g., galectin-1, galectin-3 and galectin-7); however, all galectins characterized to date lack typical secretion signal peptides. There is direct evidence that some galectins are externalized by an atypical secretory mechanism. Galectins are not unique in being secreted by atypical secretory mechanisms; other secreted proteins such as interleukin-1, thymosin and fibroblast growth factor lack signal sequences.

Galectins have been implicated in a wide variety of biological functions including cell adhesion, growth regulation, cell migration, neoplastic transformation and immune responses. Galectin-1 and -3 are the best characterized of the mammalian galectins. Galectin-1 is known to both promote and inhibit cell adhesion: in skeletal muscle, galectin-1 inhibits cell-matrix interaction and is thought to play a role in muscle development while in other cell types galectin-1 promotes cell-matrix adhesion. Galectin-1 has also been implicated in the regulation of cell proliferation and in some immune functions. Expression of galectin-1 has been shown to correlate with tumor metastasis potential (Raz, A. et al. (1986) Cancer Res. 46:3667–72).

Like galectin-1, galectin-3 inhibits cell adhesion by binding to laminin. Galectin-3 plays a role in inflammation by binding to both IgE and the IgE receptor thereby causing activation of mast cells and basophils. Galectin-3 has been shown to concentrate in the nucleus of certain cell types during proliferation. Expression of galectin-3 is elevated in certain tumors suggesting galectin-3 plays a role in metastasis; indeed overexpression of galectin-3 in a weak metastatic cell line caused a significant increase in metastatic potential (Raz, A. et al. (1990) Int. J. Cancer 46:871–77).

In rat, the expression of galectin-5 appears to be limited to blood. Although galectin-5 was originally isolated from rat lung (Cerra, R. F. et al. (1985) J. Biol. Chem. 260:10474–10477), reinvestigation showed only traces of galectin-5 in saline-perfused lung. This result led Gitt et al. (supra) to conclude that the original galectin-5 was actually isolated from blood contaminating the lung tissue. Gitt et al. (supra) propose that rat galectin-5 may possibly function in erythrocyte differentiation by mediating cell-cell adhesion during erythropoiesis.

The expression of human galectin-7 appears to be limited to keratinocytes (Magnaldo et al., supra). Galectin-7 is thought to play a role in cell-matrix and cell-cell interactions as galectin-7 is found in areas of cell-cell contact (e.g., in the upper layers of human epidermis) and its expression is sharply downregulated in anchorage independent kerati-nocytes and is absent in a malignant keratinocyte cell line. Galectin-7 may be required for the maintenance of normal keratinocytes (Madsen et al., supra).

The expression of galectin-8 is developmentally regulated in the rat suggesting that galectin-8 regulates cell growth and embryogenesis. Rat galectin-8 is expressed in a wide variety of tissues in the adult including lung, liver, kidney, spleen and muscle (cardiac and skeletal; Hadari et al., supra).

The discovery of polynucleotides encoding human galectin homologs, and the molecules themselves, provides a means to investigate cell growth and development and immune function under normal and disease conditions. Discovery of human galectin homologs satisfies a need in the art by providing new diagnostic or therapeutic compositions useful in diagnosing and treating disorders relating to aberrant hematopoiesis, immune disfunction, inflammation, or cancer.

SUMMARY OF THE INVENTION

The present invention features two novel human galectins, designated individually as GAL-5HA and GAL-5HB and collectively as GAL-5H, and characterized as having similarity to galectin-5 from rat.

Accordingly, the invention features substantially purified GAL-5H proteins GAL-5HA and GAL-5HB, having the amino acid sequences shown in SEQ ID NO:1 and SEQ ID NO:3, respectively.

One aspect of the invention features isolated and substantially purified polynucleotides that encode GAL-5H proteins GAL-5HA and GAL-5HB. In a particular aspect, the polynucleotides are the nucleotide sequences of SEQ ID NO:2 or SEQ ID NO:4, respectively.

The invention also features a polynucleotide sequence comprising the complement of SEQ ID NO:2, SEQ ID NO:4, or variants thereof. In addition, the invention features polynucleotide sequences which hybridize under stringent conditions to SEQ ID NO:2 or SEQ ID NO:4.

The invention additionally features nucleic acid sequences encoding polypeptides, oligonucleotides, peptide nucleic acids (PNA), fragments, portions or antisense molecules thereof, and expression vectors and host cells comprising polynucleotides that encode GAL-5H. The present invention also features antibodies which bind specifically to GAL-5H, and pharmaceutical compositions comprising substantially purified GAL-5H. The invention also features the use of agonists and antagonists of GAL-5H.

BRIEF DESCRIPTION OF THE FIGURES

FIG. 1 shows the amino acid sequence (SEQ ID NO:1) and nucleic acid sequence (SEQ ID NO:2) of GAL-5HA. The alignment was produced using MACDNASIS PRO™ software (Hitachi Software Engineering Co., Ltd., San Bruno, Calif.).

FIGS. 2A and 2B show the amino acid sequence (SEQ ID NO:3) and nucleic acid sequence (SEQ ID NO:4) of GAL-5HB.

FIG. 3 shows the amino acid sequence alignment between GAL-5HA (SEQ ID NO:1) and galectin-5 from rat (GI 727176; SEQ ID NO:5). The alignment was produced using the multisequence alignment program of DNASTAR™ software (DNASTAR Inc, Madison Wis.).

FIG. 4 shows the amino acid sequence alignment between GAL-5HB (SEQ ID NO:3) and galectin-5 from rat (GI 727176; SEQ ID NO:5).

DESCRIPTION OF THE INVENTION

Figure 5A:
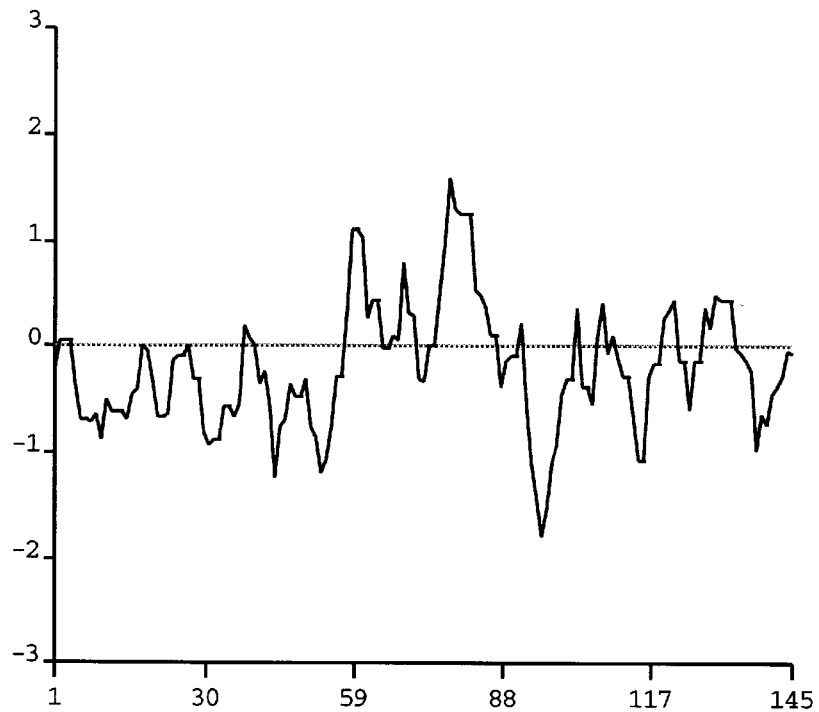
FIGS. 5A and 5B show the hydrophobicity plots (MACDNASIS PRO software) for GAL-5HA, SEQ ID NO:1, and rat galectin-5, SEQ ID NO:5, respectively; the positive X axis reflects amino acid position, and the negative Y axis, hydrophobicity.

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

"Nucleic acid sequence", as used herein, refers to an oligonucleotide, nucleotide, or polynucleotide, and fragments or portions thereof, and to DNA or RNA of genomic or synthetic origin which may be single- or double-stranded and represent the sense or antisense strand. Similarly, "amino acid sequence" as used herein refers to an oligopeptide, peptide, polypeptide, or protein sequence, and fragments or portions thereof, and to naturally occurring or synthetic molecules.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

GAL-5H, as used herein, refers to the amino acid sequences of substantially purified GAL-5H obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR™ (Perkin Elmer, Norwalk, Conn.) in the 5' and/or the 3' direction and resequenced, or which has been assembled from the overlapping sequences of more than one Incyte clone using the GELVIEW™ Fragment Assembly system (GCG, Madison, Wis.), or which has been both extended and assembled.

A "variant" of GAL-5H, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic GAL-5H, or any oligopeptide thereof, to induce a specific immune response in appropriate animals or cells and to bind with specific antibodies.

The term "agonist", as used herein, refers to a molecule which, when bound to GAL-5H, causes a change in GAL-5H which modulates the activity of GAL-5H. Agonists may include proteins, nucleic acids, carbohydrates, or any other molecules which bind to GAL-5H.

The terms "antagonist" or "inhibitor", as used herein, refer to a molecule which, when bound to GAL-5H, blocks or modulates the biological or immunological activity of GAL-5H. Antagonists and inhibitors may include proteins, nucleic acids, carbohydrates, or any other molecules which bind to GAL-5H.

The term "modulate", as used herein, refers to a change or an alteration in the biological activity of GAL-5H. Modulation may be an increase or a decrease in protein activity, a change in binding characteristics, or any other change in the biological, functional or immunological properties of GAL-5H.

The term "mimetic", as used herein, refers to a molecule, the structure of which is developed from knowledge of the structure of GAL-5H or portions thereof and, as such, is able to effect some or all of the actions of galectin-like molecules.

The term "derivative", as used herein, refers to the chemical modification of a nucleic acid encoding GAL-5H or the encoded GAL-5H. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) PCR *Primer, a Laboratory Manual*, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm–5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human GAL-5HA and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding GAL-5H or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2 or SEQ ID NO:4 by northern analysis is indicative of the presence of mRNA encoding GAL-5H in a sample and thereby correlates with expression of the transcript from the polynucleotide encoding the protein.

"Alterations" in the polynucleotide of SEQ ID NO:2 or SEQ ID NO:4, as used herein, comprise any alteration in the sequence of polynucleotides encoding GAL-5H including deletions, insertions, and point mutations that may be detected using hybridization assays. Included within this definition is the detection of alterations to the genomic DNA sequence which encodes GAL-5H (e.g., by alterations in the pattern of restriction fragment length polymorphisms capable of hybridizing to), the inability of a selected fragment of SEQ ID NO:2 or SEQ ID NO:4 to hybridize to a sample of genomic DNA (e.g., using allele-specific oligonucleotide probes), and improper or unexpected hybridization, such as hybridization to a locus other than the normal chromosomal locus for the polynucleotide sequence encoding GAL-5H (e.g., using fluorescent in situ hybridization (FISH) to metaphase chromosome spreads).

As used herein, the term "antibody" refers to intact molecules as well as fragments thereof, such as Fa, F(ab')$_2$, and Fv, which are capable of binding the epitopic determinant. Antibodies that bind GAL-5H polypeptides can be prepared using intact polypeptides or fragments containing small peptides of interest as the immunizing antigen. The polypeptide or peptide used to immunize an animal can be derived from the translation of mRNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

THE INVENTION

The invention is based on the discovery of two novel human galectins (GAL-5HA and GAL-5HB, collectively referred to as GAL-5H), the polynucleotides encoding GAL-5H, and the use of these compositions for the diagnosis, prevention, or treatment of diseases relating to aberrant hematopoiesis, immune disfunction, inflammation, or cancer.

Nucleic acids encoding the human GAL-5HA of the present invention were first identified in Incyte Clone 319912 from a peripheral blood cell cDNA library (EOSHET02) through a computer-generated search for amino acid sequence alignments. A consensus sequence, SEQ ID NO:2, was derived from the following overlapping and/or extended nucleic acid sequences: Incyte Clones 319912 (EOSIHET02); 584880 and 585041 (PROSNOT02); 731497 (LUNGNOT03); and 775761 (COLNNOT05).

Nucleic acid sequence encoding the human GAL-5HB of the present invention were first identified in Incyte Clone 540284 from a lymph node tissue cDNA library (LNODNOT02) through a computer-generated search for amino acid sequence alignments. A consensus sequence, SEQ ID NO:4, was derived from the following overlapping and/or extended nucleic acid sequences: Incyte Clones 286802, 319912, and 334602 (EOSIHET02); 479550 (MMLR2DT01); 518864 (MMLR1DT01); 540284 (LNODNOT02); 585041 (PROSNOT02); and 1221325 (NEUTGMT01).

Figure 5B:
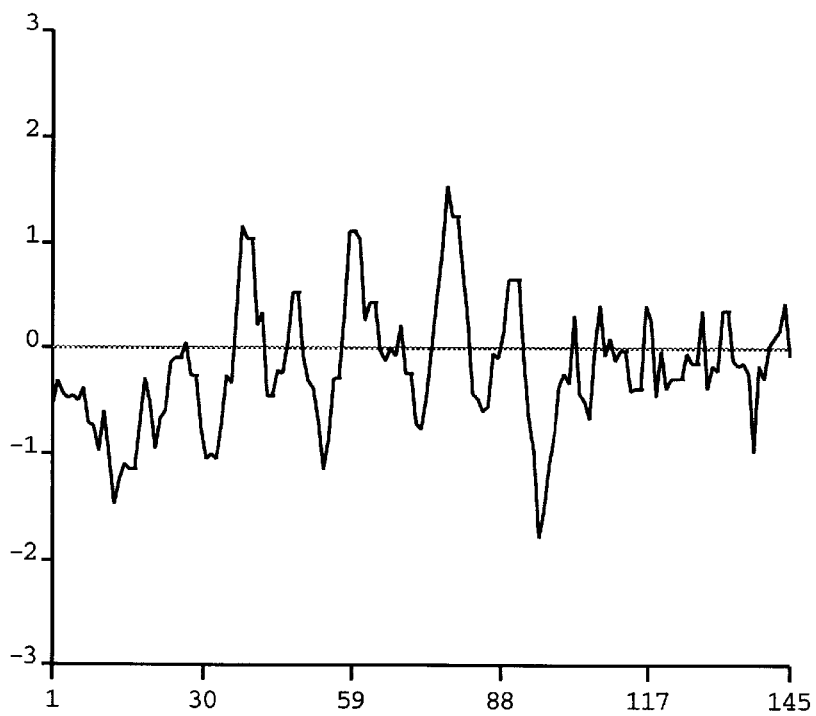

In one embodiment, the invention encompasses a polypeptide comprising the amino acid sequence of SEQ ID NO:1, as shown in FIG. 1. GAL-5HA is 145 amino acids in length and contains the CRD sequence motif conserved in all known galectins, which corresponds to $G_{25}$ $H_{57}$ $N_{59}$ $P_{60}$ $R_{61}$ $V_{68}$ $N_{70}$ $W_{77}$ $E_{80}$ $F_{90}$ $G_{93}$ $R_{122}$ in SEQ ID NO:1. GAL-5HA has chemical and structural homology with rat galectin-5 (GI 727176; SEQ ID NO:5). In particular, GAL-5HA and rat galectin-5 share 68% amino acid sequence identity (FIG. 3). As illustrated by FIGS. 5A and 5B, GAL-5HA and rat galectin-5 have similar hydrophobicity plots.

Figure 6A:
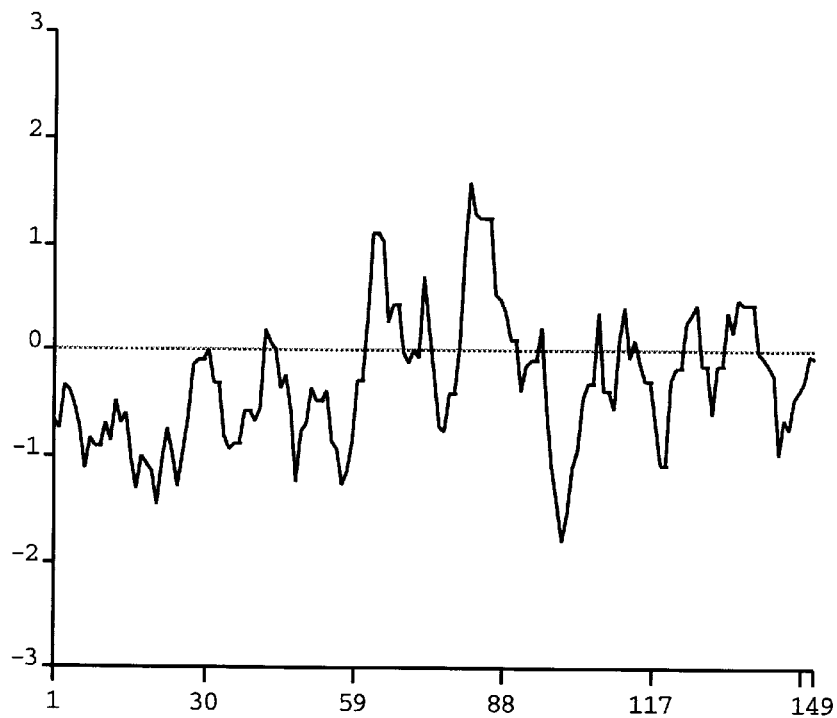
FIGS. 6A and 6B show the hydrophobicity plots for GAL-5HB, SEQ ID NO:3, and rat galectin-5, SEQ ID NO:5, respectively.
Figure 6B:
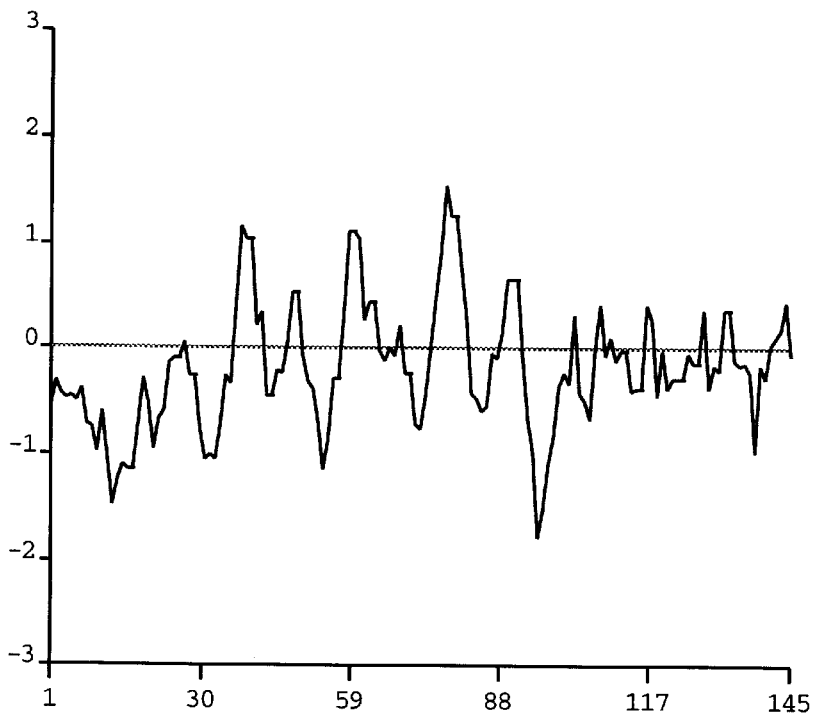

In another embodiment, the invention encompasses a polypeptide comprising the amino acid sequence of SEQ ID NO:3, as shown in FIGS. 2A and 2B. GAL-5HB is 149 amino acids in length and contains the CRD sequence motif conserved in all known galectins, which corresponds to $G_{39}$ $H_{61}$ $N_{63}$ $P_{64}$ $R_{65}$ $V_{72}$ $N_{74}$ $W_{81}$ $E_{84}$ $F_{94}$ $G_{97}$ $R_{126}$ in SEQ ID NO:3. GAL-5HB has chemical and structural homology with rat galectin-5 (GI 727176; SEQ ID NO:5). In particular, GAL-5HB and rat galectin-5 share 72% amino acid sequence identity (FIG. 4). As illustrated by FIGS. 6A and 6B, GAL-5HB and rat galectin-5 have similar hydrophobicity plots. The 3' untranslated region of the GAL-5HB cDNA (SEQ ID NO:4) is over 500 nucleotides in length and may play a role in the translational regulation of GAL-5HB.

GAL-5HA and GAL-5HB share 88% amino acid sequence identity and differ primarily in the N-terminal amino acid sequence upstream of the CRD. The difference in GAL-5HA and GAL-5HB N-terminal amino acid sequences appears to have significance in the types of interactions mediated by these two molecules.

Northern analysis shows the expression of GAL-5H in various libraries, with the most abundant expression found in libraries derived from hematopoietic cells, including leukocytes, promonocytes, macrophages, eosinophils, lymphocytes, and granulocytes. GAL-5H is also found in lymphoid tissues including spleen, liver, and lymph nodes; tissues associated with inflammation, including ileum and colon (ulcerative colitis, Crohn's disease and polyps), synovium (rheumatoid and osteoarthritis), lung (asthma) and skin (erythema nodosum); and malignant or tumor-associated tissues including prostate, pancreas, lung, colon, tongue, brain, breast, bladder, adrenal gland, uterus, ovary, and stomach.

The invention also encompasses GAL-5H variants. A preferred GAL-5H variant is one having at least 80%, and more preferably 90%, amino acid sequence similarity to the GAL-5H amino acid sequence (SEQ ID NO:1 or SEQ ID NO:3). A most preferred GAL-5H variant is one having at least 95% amino acid sequence similarity to SEQ ID NO:1 or SEQ ID NO:3.

The invention also encompasses polynucleotides which encode GAL-5H. Accordingly, any nucleic acid sequence which encodes the amino acid sequence of GAL-5H can be used to generate recombinant molecules which express GAL-5H. In a particular embodiment, the invention encompasses the polynucleotide comprising the nucleic acid of SEQ ID NO:2 or SEQ ID NO:4 as shown in FIG. 1 and FIGS. 2A and 2B.

It will be appreciated by those skilled in the art that as a result of the degeneracy of the genetic code, a multitude of nucleotide sequences encoding GAL-5H, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring GAL-5H, and all such variations are to be considered as being specifically disclosed.

Although nucleotide sequences which encode GAL-5H and its variants are preferably capable of hybridizing to the nucleotide sequence of the naturally occurring GAL-5H under appropriately selected conditions of stringency, it may be advantageous to produce nucleotide sequences encoding GAL-5H or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding GAL-5H and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode GAL-5H and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding GAL-5H or any portion thereof.

Also encompassed by the invention are polynucleotide sequences that are capable of hybridizing to the claimed nucleotide sequences, and in particular, those shown in SEQ ID NO:2 or SEQ ID NO:4, under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–11), and may be used at a defined stringency.

Altered nucleic acid sequences encoding GAL-5H which are encompassed by the invention include deletions, insertions, or substitutions of different nucleotides resulting in a polynucleotide that encodes the same or a functionally equivalent GAL-5H. The encoded protein may also contain deletions, insertions, or substitutions of amino acid residues which produce a silent change and result in a functionally equivalent GAL-5H. Deliberate amino acid substitutions may be made on the basis of similarity in polarity, charge, solubility, hydrophobicity, hydrophilicity, and/or the amphipathic nature of the residues as long as the biological activity of GAL-5H is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the gene encoding GAL-5H. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, SEQUENASE® (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

The nucleic acid sequences encoding GAL-5H may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO® 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER™ libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER™ and SEQUENCE NAVIGATOR™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode GAL-5H, or fusion proteins or functional equivalents thereof, may be used in recombinant DNA molecules to direct expression of GAL-5H in appropriate host cells. Due to the inherent degeneracy of the genetic code, other DNA sequences which encode substantially the same or a functionally equivalent amino acid sequence may be produced and these sequences may be used to clone and express GAL-5H.

As will be understood by those of skill in the art, it may be advantageous to produce GAL-5H-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter sequences encoding GAL-5H for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, to alter glycosylation patterns, to change codon preference, to produce splice variants, or to introduce mutations, and so forth.

In another embodiment of the invention, natural, modified, or recombinant polynucleotides encoding GAL-5H may be ligated to a heterologous sequence to encode a fusion protein. For example, to screen peptide libraries for inhibitors of GAL-5H activity, it may be useful to encode a chimeric GAL-5H protein that can be recognized by a commercially available antibody. A fusion protein may also be engineered to contain a cleavage site located between a sequence encoding GAL-5H and the heterologous protein sequence, so that GAL-5H may be cleaved and purified away from the heterologous moiety.

In another embodiment, sequences encoding GAL-5H may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of GAL-5H, or a portion thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of GAL-5H, or any part thereof, may be altered during direct synthesis and/or combined using chemical methods with sequences from other proteins, or any part thereof, to produce a variant polypeptide.

In order to express a biologically active GAL-5H, the nucleotide sequences encoding GAL-5H or functional equivalents, may be inserted into appropriate expression vectors, i.e., a vector which contains the necessary elements for the transcription and translation of the inserted coding sequence.

Methods which are well known to those skilled in the art may be used to construct expression vectors containing sequences encoding GAL-5H and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding GAL-5H. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT® phagemid (Stratagene, LaJolla, Calif.) or PSPORT™ plasmid (Gibco BRL), and the like, may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding GAL-5H, vectors based on SV40 or EBV may be used with an appropriate selectable marker.

In bacterial systems, a number of expression vectors may be selected depending upon the use intended for GAL-5H. For example, when large quantities of GAL-5H are needed for the induction of antibodies, vectors which direct high level expression of fusion proteins that are readily purified may be used. Such vectors include, but are not limited to, the multifunctional *E. coli* cloning and expression vectors such as BLUESCRIPT® (Stratagene), in which the sequence encoding GAL-5H may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of a sequence encoding GAL-5H may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196).

An insect system may also be used to express GAL-5H. For example, in one such system, *Autographa californica* nuclear polyhedrosis virus (AcNPV) is used as a vector to express foreign genes in *Spodoptera frugiperda* cells or in Trichoplusia larvae. The sequences encoding GAL-5H may be cloned into a non-essential region of the virus, such as the polyhedrin gene, and placed under control of the polyhedrin promoter. Successful insertion of GAL-5H will render the polyhedrin gene inactive and produce recombinant virus lacking coat protein. The recombinant viruses may then be used to infect, for example, *S. frugiperda* cells or Trichoplusia larvae in which GAL-5H may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding GAL-5H may be ligated into an adenovirus transcription/translation complex consisting of the late promoter and tripartite leader sequence. Insertion in a non-essential E1 or E3 region of the viral genome may be used to obtain a viable virus which is capable of expressing GAL-5H in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding GAL-5H. Such signals include the ATG initiation codon and adjacent sequences. In cases where sequences encoding GAL-5H, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express GAL-5H may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk or aprt cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins. β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding GAL-5H is inserted within a marker gene sequence, recombinant cells containing sequences encoding GAL-5H can be identified by the absence of marker gene function. Alternatively, a marker gene can be placed in tandem with a sequence encoding GAL-5H under the control of a single promoter. Expression of the marker gene in response to induction or selection usually indicates expression of the tandem gene as well.

Alternatively, host cells which contain sequences encoding and expressing GAL-5H may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of the nucleic acid or protein.

The presence of polynucleotide sequences encoding GAL-5H can be detected by DNA-DNA or DNA-RNA hybridization or amplification using probes or portions or fragments of polynucleotides encoding GAL-5H. Nucleic acid amplification based assays involve the use of oligonucleotides or oligomers based on the sequences encoding GAL-5H to detect transformants containing DNA or RNA encoding GAL-5H. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of GAL-5H, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on GAL-5H is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:121 1–1216).

A wide variety of labels and conjugation techniques are known by those skilled in the art and may be used in various nucleic acid and amino acid assays. Means for producing labeled hybridization or PCR probes for detecting sequences related to polynucleotides encoding GAL-5H include oligolabeling, nick translation, end-labeling or PCR amplification using a labeled nucleotide. Alternatively, sequences encoding GAL-5H, or any portion thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits from Pharmacia & Upjohn (Kalamazoo, Mich.); Promega (Madison, Wis.); and U.S. Biochemical Corp. (Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding GAL-5H may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode GAL-5H may be designed to contain signal sequences which direct secretion of GAL-5H through a prokaryotic or eukaryotic cell membrane. Other recombinant constructions may be used to join sequences encoding GAL-5H to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and GAL-5H may be used to facilitate purification. One such expression vector provides for expression of a fusion protein containing GAL-5H and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3: 263–281) while the enterokinase cleavage site provides a means for purifying GAL-5H from the fusion protein. A discussion of vectors which contain fusion proteins is provided in Kroll, D. J. et al. (1993; DNA Cell Biol. 12:441–453).

In addition to recombinant production, fragments of GAL-5H may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of GAL-5H may be chemically synthesized separately and combined using chemical methods to produce the full length molecule.

THERAPEUTICS

Chemical and structural homology exists between GAL-5HA, GAL-5HB, and rat galectin-5. In addition, GAL-5H is expressed in hematopoietic cells and tissues, lymphoid tissues, and secretory tissues. Therefore, GAL-5H appears to play a role in cell growth and development and in the modulation of immune and inflammatory responses.

Therefore, in one embodiment, GAL-5H or a fragment or derivative thereof may be used to treat cells in vivo or ex vivo for the purposes of tissue or organ regeneration. This embodiment would be of particular benefit in the proliferation and differentiation of hematopoietic, epithelial, or secretory cells.

In another embodiment, a vector capable of expressing GAL-5H, or a fragment or derivative thereof, may also be administered to a cell culture or a subject for ex vivo or in vivo therapy as described above.

In another embodiment, a vector expressing antisense of the polynucleotide encoding GAL-5H may be administered to a subject to treat or prevent a disorder which is associated with expression of GAL-5H. Such disorders may include, but are not limited to, inflammatory and allergic conditions such as rheumatoid and osteoarthritis, asthma, allergic rhinitis, atopic dermatitis; autoimmune conditions such as Sjögren's syndrome, scleroderma, hyperthyroidism (Grave's disease), systemic lupus, myasthenia gravis, autoimmune thyroiditis, diabetes mellitus, pancreatitis, ulcerative colitis, Crohn's disease, atrophic gastritis, and graft-vs-host disease; disorders relating to abnormal cellular differentiation, proliferation, or degeneration, including hyperaldosteronism, hypocortisolism (Addison's disease), hypothyroidism, colorectal polyps, gastric and duodenal ulcers, cancers of hematopoietic cells and lymphoid tissues including leukemias, lymphomas (including Hodgkin's disease), lymphosarcomas and myelomas, and cancers of glands, tissues, and organs involved in secretion or absorption, including prostate, pancreas, lung, tongue, brain, breast, and bladder, adrenal gland, thyroid, liver, uterus, kidney, testes, and organs of the gastrointestinal tract including small intestine, colon, rectum, and stomach.

In another embodiment, antagonists or inhibitors of GAL-5H may be administered to a subject to treat or prevent any of the disorders described above. In a particular aspect, antibodies which are specific for GAL-5H may be used directly as an antagonist, or indirectly as a targeting or delivery mechanism for bringing a pharmaceutical agent to cells or tissue which express GAL-5H.

In other embodiments, any of the therapeutic proteins, antagonists, antibodies, agonists, antisense sequences or vectors described above may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of GAL-5H may be produced using methods which are generally known in the art. In particular, purified GAL-5H may be used to produce antibodies or to screen libraries of pharmaceutical agents to identify those which specifically bind GAL-5H.

Antibodies specific for GAL-5H may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with GAL-5H or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to GAL-5H have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of GAL-5H amino acids may be fused with those of another protein such as keyhole limpet hemocyanin and antibody produced against the chimeric molecule.

Monoclonal antibodies to GAL-5H may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J Immunol. Methods 81:31–42; Cote, R. J. et al. (1983) Proc. Natl. Acad. Sci. 80:2026–2030; Cole, S. P. et al. (1985) Mol Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–55; Neuberger, M. S. et al. (1984) Nature 312:604–8; Takeda, S. et al. (1985) Nature 314:452–4). Alternatively, techniques described for the production of single chain antibodies may be adapted, using methods known in the art, to produce GAL-5H-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86: 3833–37; Winter, G. et al. (1991) Nature 349:293–9).

Antibody fragments which contain specific binding sites for GAL-5H may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–81).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between GAL-5H and its specific antibody. A two-site, monoclonal-based immunoassay utilizing monoclonal antibodies reactive to two non-interfering GAL-5H epitopes is preferred, but a competitive binding assay may also be employed (Maddox, supra).

In another embodiment of the invention, the polynucleotides encoding GAL-5H, or any fragment thereof, or antisense molecules, may be used for therapeutic purposes. In one aspect, antisense to the polynucleotide encoding GAL-5H may be used in situations in which it would be desirable to block the transcription of mRNA. In particular, cells may be transformed with sequences complementary to polynucleotides encoding GAL-5H. Thus, antisense sequences may be used to modulate GAL-5H activity, or to achieve regulation of gene function. Such technology is now well known in the art, and sense or antisense oligomers or larger fragments, can be designed from various locations along the coding or control regions of sequences encoding GAL-5H.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense polynucleotides of the gene encoding GAL-5H. These techniques are described both in Sambrook et al. (supra) and in Ausubel et al. (supra).

Genes encoding native GAL-5H can be turned off by transforming a cell or tissue with expression vectors which express high levels of the polynucleotide, or fragment thereof, which encodes GAL-5H. Such constructs may be used to introduce untranslatable sense or antisense sequence into a cell. Even in the absence of integration into the genomic DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding GAL-5H, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding GAL-5H.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding GAL-5H. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of GAL-5H, antibodies to GAL-5H, mimetics, agonists, antagonists, or inhibitors of GAL-5H. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of GAL-5H, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example GAL-5H or fragments thereof, antibodies of GAL-5H, agonists, antagonists or inhibitors of GAL-5H, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind GAL-5H may be used for the diagnosis of conditions or diseases characterized by expression of GAL-5H, or in assays to monitor patients being treated with GAL-5H, agonists, antagonists or inhibitors. The antibodies useful for diagnostic purposes may be prepared in the same manner as those described above for therapeutics. Diagnostic assays for GAL-5H include methods which utilize the antibody and a label to detect GAL-5H in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring GAL-5H are known in the art and provide a basis for diagnosing altered or abnormal levels of GAL-5H expression. Normal or standard values for GAL-5H expression are established by combining body fluids or cell extracts taken from normal mammalian subjects, preferably human, with antibody to GAL-5H under conditions suitable for complex formation. The amount of standard complex formation may be quantified by various methods, but preferably by photometric, means. Quantities of GAL-5H expressed in subject, control, and disease, samples from biopsied tissues are compared with the standard values. Deviation between standard and subject values establishes the parameters for diagnosing disease.

In another embodiment of the invention, the polynucleotides encoding GAL-5H may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of GAL-5H may be correlated with disease. The diagnostic assay may be used to distinguish between absence, presence, and excess expression of GAL-5H, and to monitor regulation of GAL-5H levels during therapeutic intervention.

In one aspect, hybridization with PCR probes which are capable of detecting polynucleotide sequences, including genomic sequences, encoding GAL-5H or closely related molecules, may be used to identify nucleic acid sequences which encode GAL-5H. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding GAL-5H, alleles, or related sequences.

Probes may also be used for the detection of related sequences, and should preferably contain at least 50% of the nucleotides from any of the sequences encoding GAL-5H. The hybridization probes of the subject invention may be DNA or RNA and derived from the nucleotide sequences of SEQ ID NO:2 or SEQ ID NO:4 or from genomic sequence including promoter, enhancer elements, and introns of the naturally occurring GAL-5H.

Means for producing specific hybridization probes for DNAs encoding GAL-5H include the cloning of nucleic acid sequences encoding GAL-5H or GAL-5H derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding GAL-5H may be used for the diagnosis of disorders which are associated with expression of GAL-5H. Examples of such disorders include, but are not limited to, inflammatory and allergic conditions such as rheumatoid and osteoarthritis, asthma, allergic rhinitis, atopic dermatitis; autoimmune conditions such as Sjögren's syndrome, scleroderma, hyperthyroidism (Grave's disease), systemic lupus, myasthenia gravis, autoimmune thyroiditis, diabetes mellitus, pancreatitis, ulcerative colitis, Crohn's disease, atrophic gastritis, and graft-vs-host disease; cancers of hematopoietic cells and lymphoid tissues including leukemias, lymphomas (including Hodgkin's disease), lymphosarcomas and myelomas; cancers of glands, tissues, and organs involved in secretion or absorption, including prostate, pancreas, lung, tongue, brain, breast, and bladder, adrenal gland, thyroid, liver, uterus, kidney, and testes, and organs of the gastrointestinal tract including small intestine, colon, rectum, and stomach; other disorders relating to abnormal cellular differentiation, proliferation, or degeneration, including hyperaldosteronism, hypocortisolism (Addison's disease), hypothyroidism, colorectal polyps, and gastric and duodenal ulcers. The polynucleotide sequences encoding GAL-5H may be used in Southern or northern analysis, dot blot, or other membrane-based technologies; in PCR technologies; or in dip stick, pin, ELISA or chip assays utilizing fluids or tissues from patient biopsies to detect altered GAL-5H expression. Such qualitative or quantitative methods are well known in the art.

In a particular aspect, the nucleotide sequences encoding GAL-5H may be useful in assays that detect activation or induction of various cancers, particularly those mentioned above. The nucleotide sequences encoding GAL-5H may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding GAL-5H in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of GAL-5H, a normal or standard profile for expression is established. This may be accomplished by combining body fluids or cell extracts taken from normal subjects, either animal or human, with a sequence, or a fragment thereof, which encodes GAL-5H, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of an abnormal amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding GAL-5H may involve the use of PCR. Such oligomers may be chemically synthesized, generated enzymatically, or produced from a recombinant source. Oligomers will preferably consist of two nucleotide sequences, one with sense orientation (5'->3') and another with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of GAL-5H include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequence which encodes GAL-5H may also be used to generate hybridization probes which are useful for mapping the naturally occurring genomic sequence. The sequence may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma, R. S. et al. (1988) *Human Chromosomes: A Manual of Basic Techniques*, Pergamon Press, New York, N.Y.) may be correlated with other physical chromosome mapping techniques and genetic map data. Examples of genetic map data can be found in the 1994 Genome Issue of Science (265:1981 f). Correlation between the location of the gene encoding GAL-5H on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, GAL-5H, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between GAL-5H and the agent being tested, may be measured.

Another technique for drug screening which may be used provides for high throughput screening of compounds having suitable binding affinity to the protein of interest as described in published PCT application WO84/03564. In this method, as applied to GAL-5H, large numbers of different small test compounds are synthesized on a solid substrate, such as plastic pins or some other surface. The test compounds are reacted with GAL-5H, or fragments thereof, and washed. Bound GAL-5H is then detected by methods well known in the art. Purified GAL-5H can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding GAL-5H specifically compete with a test compound for binding GAL-5H. In this manner, the antibodies can be used to detect the presence of any peptide which shares one or more antigenic determinants with GAL-5H.

In additional embodiments, the nucleotide sequences which encode GAL-5H may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction

EOSIHET02

The eosinophils used for this library were obtained via aphoresis of a 56 year old Caucasian male patient at Mayo Clinic (Rochester Minn.) who had been diagnosed with hypereosinophilic syndrome. The cells were washed twice in phosphate buffered saline and lysed immediately in a buffer containing guanidinium isothiocyanate. The lysate was extracted twice with phenol chloroform and centrifuged over a CsCl cushion using a Beckman SW28 rotor and a Beckman L8–70M Ultracentrifuge (Beckman Instruments). The RNA was precipitated using 0.3M sodium acetate and 2.5 volumes of ethanol, resuspended in water and DNase treated for 15 min at 37° C. The RNA was isolated using the QIAGEN OLIGOTEX kit (QIAGEN Inc, Chatsworth Calif.). Custom cDNA library construction was performed by Stratagene (La Jolla Calif.).

First strand cDNA synthesis was accomplished using an oligo d(T) primer/linker which also contained an XhoI restriction site. Second strand synthesis was performed using a combination of DNA polymerase I, E. coli ligase and RNAse H, followed by the addition of an EcoRI adaptor to the blunt ended cDNA. The EcoRI adapted, double-stranded cDNA was then digested with XhoI restriction enzyme and fractionated to obtain sequences which exceeded 800 bp in size. The cDNAs were inserted into the LAMBDAZAP® vector system (Stratagene); then the vector which contains the PBLUESCRIPT™ phagemid (Stratagene) was transformed into E. coli host cells strain XL1-BLUEMRF™ (Stratagene).

The phagemid forms of individual cDNA clones were obtained by the in vivo excision process. Enzymes from both PBLUESCRIPT and a cotransformed f1 helper phage nicked the DNA, initiated new DNA synthesis, and created the smaller, single-stranded circular phagemid molecules which contained the cDNA insert. The phagemid DNA was released, purified, and used to reinfect fresh host cells (SOLR, Stratagene). Presence of the phagemid which carries the gene for β-lactamase allowed transformed bacteria to grow on medium containing ampicillin.

LNODNOT02

The LNODNOT02 cDNA library was constructed from lymph node tissue removed from a 42 year old, Caucasian female (lot #RA95-05-0297) obtained from the Keystone Skin Bank (International Institute for Advanced Medicine, Exton, Pa.). The tissue was flash frozen, ground in a mortar and pestle, and lysed immediately in a buffer containing guanidinium isothiocyanate. The lysate was extracted twice with acid phenol, pH 4.0, and centrifuged over a CsCl cushion using a Beckman SW28 rotor in a L8–70M Ultracentrifuge (Beckman Instruments). The RNA was precipitated from 0.3M sodium acetate using 2.5 volumes of ethanol, resuspended in water and DNase treated for 15 min at 37° C. The poly (A+) RNA was isolated using the QIAGEN OLIGOTEX kit (QIAGEN Inc.) and used to construct the cDNA library.

The RNA was handled according to the recommended protocols in the SuperScript Plasmid System (catalog #18248-013; Gibco/BRL). The cDNAs were ligated into the vector PSPORT1, and the plasmid was subsequently transformed into DH5α™ competent cells (Cat. #18258-012, Gibco/BRL).

II Isolation and Sequencing of cDNA Clones

Plasmid DNA was released from the cells and purified using the Miniprep Kit (Catalogue #77468; Advanced Genetic Technologies Corporation, Gaithersburg Md.). This kit consists of a 96 well block with reagents for 960 purifications. The recommended protocol was employed except for the following changes: 1) the 96 wells were each filled with only 1 ml of sterile Terrific Broth (Catalog #22711, LIFE TECHNOLOGIES™, Gaithersburg Md.) with carbenicillin at 25 mg/L and glycerol at 0.4%; 2) the bacteria were cultured for 24 hours after the wells were inoculated and then lysed with 60$\mu$l of lysis buffer; 3) a centrifugation step employing the Beckman GS-6R @2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

Alternative methods of purifying plasmid DNA include the use of MAGIC MINIPREPS™ DNA Purification System (Catalogue #A7100, Promega) or QIAWELL™-8 Plasmid, QIAWELL PLUS DNA and QIAWELL ULTRA DNA Purification Systems (QIAGEN, Inc.).

The cDNAs were sequenced by the method of Sanger F. and A. R. Coulson (1975; J. Mol. Biol. 94:441f), using a Hamilton Micro Lab 2200 (Hamilton, Reno Nev.) in combination with four Peltier Thermal Cyclers (PTC200 from MJ Research, Watertown Mass.) and Applied Biosystems 377 or 373 DNA Sequencing Systems (Perkin Elmer) and reading frame was determined.

III Homology Searching of cDNA Clones and Their Deduced Proteins

Each cDNA was compared to sequences in GenBank using a search algorithm developed by Applied Biosystems and incorporated into the INHERIT™ 670 sequence analysis system. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 sequence analysis system using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul, S. F. (1993) J. Mol. Evol. 36:290–300; Altschul, S. F. et al. (1990) J. Mol. Biol. 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding GAL-5H occurs. Abundance and percent abundance are also reported. Abundance directly reflects the number of times a particular transcript is represented in a cDNA library, and percent abundance is abundance divided by the total number of sequences examined in the cDNA library.

V Extension of Polynucleotides Encoding GAL-5H to Full Length or to Recover Regulatory Sequences Polynucleotides encoding GAL-5H (SEQ ID NO:2 or SEQ ID NO:4) are used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward", generating amplicons containing new, unknown nucleotide sequence for the region of interest. The initial primers are designed from the cDNA using OLIGO 4.06 (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M. J. Research, Watertown, Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat step 4–6 for 15 additional cycles
Step 8 94° C. for 15 sec
Step 9 65° C. for 1 min
Step 10 68° C. for 7:15 min
Step 11 Repeat step 8–10 for 12 cycles
Step 12 72° C. for 8 min
Step 13 4° C. (and holding)

A 5–10 µl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQUICK Kit (Qiagen Inc.). After recovery of the DNA, Klenow enzyme is used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent *E. coli* cells (in 40 µl of appropriate media) are transformed with 3 µl of ligation mixture and cultured in 80 µl of SOC medium (Sambrook et al., supra). After incubation for one hour at 37° C., the whole transformation mixture is plated on Luria Bertani (LB)-agar (Sambrook et al., supra) containing 2× Carb. The following day, several colonies are randomly picked from each plate and cultured in 150 µl of liquid LB/2× Carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer, and one or both of the gene specific primers used for the extension reaction are added to each well. Amplification is performed using the following conditions:

Step 1 94° C. for 60 sec
Step 2 94° C. for 20 sec
Step 3 55° C. for 30 sec
Step 4 72° C. for 90 sec
Step 5 Repeat steps 2–4 for an additional 29 cycles
Step 6 72° C. for 180 sec
Step 7 4° C. (and holding)

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2 or SEQ ID NO:4 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 $\mu$Ci of [$\gamma$-$^{32}$P] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Antisense Molecules

Antisense molecules to the sequence encoding GAL-5H, or any part thereof, is used to inhibit in vivo or in vitro expression of naturally occurring GAL-5H. Although use of antisense oligonucleotides, comprising about 20 base-pairs, is specifically described, essentially the same procedure is used with larger cDNA fragments. An oligonucleotide based on the sequences encoding GAL-5H is used to inhibit expression of naturally occurring GAL-5H. The complementary oligonucleotide is designed from the most unique 5' sequence as shown and used either to inhibit transcription by preventing promoter binding to the upstream nontranslated sequence or translation of a transcript encoding GAL-5H by preventing the ribosome from binding. Using an appropriate portion of the signal and 5' sequence of SEQ ID NO:2 or SEQ ID NO:4, an effective antisense oligonucleotide includes any 15–20 nucleotides spanning the region which translates into the signal or 5' coding sequence of the polypeptide as shown in FIG. 1 and FIGS. 2A and 2B.

VIII Expression of GAL-5H

Expression of GAL-5H is accomplished by subcloning the cDNAs into appropriate vectors and transforming the vectors into host cells. In this case, the cloning vector, PSPORT, previously used for the generation of the cDNA library is used to express GAL-5H in E. coli. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of GAL-5H into the bacterial growth media which can be used directly in the following assay for activity.

IX Demonstration of GAL-5H Activity

The ability of GAL-5H to bind to β-galactoside sugars is examined as follows. The GAL-5H protein is applied to a lactosyl-Sepharose column, and the column is eluted with 0.1M lactose. The presence of a protein having the size expected for GAL-5H in the elute indicates the ability of the recombinant GAL-5H to bind β-galactoside sugars. Alternative methods for accessing the ability of the recombinant GAL-5H to bind lactose are known in the art (see, for example, the binding of recombinant galectins with immobilized asialofeutin in the presence or absence of 150 mM lactose described by Madsen P. et al., supra).

X Production of GAL-5H Specific Antibodies

GAL-5H that is substantially purified using PAGE electrophoresis (Sambrook, supra), or other purification techniques, is used to immunize rabbits and to produce antibodies using standard protocols. The amino acid sequence deduced from SEQ ID NO:2 or SEQ ID NO:4 is analyzed using DNASTAR software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring GAL-5H Using Specific Antibodies

Naturally occurring or recombinant GAL-5H is substantially purified by immunoaffinity chromatography using antibodies specific for GAL-5H. An immunoaffinity column is constructed by covalently coupling GAL-5H antibody to an activated chromatographic resin, such as CnBr-activated Sepharose (Pharmacia & Upjohn). After the coupling, the resin is blocked and washed according to the manufacturer's instructions.

Media containing GAL-5H is passed over the immunoaffinity column, and the column is washed under conditions that allow the preferential absorbance of GAL-5H (e.g., high ionic strength buffers in the presence of detergent). The column is eluted under conditions that disrupt antibody/GAL-5H binding (eg, a buffer of pH 2–3 or a high concentration of a chaotrope, such as urea or thiocyanate ion), and GAL-5H is collected.

XII Identification of Molecules Which Interact with GAL-5H

GAL-5H or biologically active fragments thereof are labeled with $^{125}$I Bolton-Hunter reagent (Bolton, A. E. and W. M. Hunter (1973) Biochem. J. 133: 529–39). Candidate molecules previously arrayed in the wells of a multi-well plate are incubated with the labeled GAL-5H, washed and any wells with labeled GAL-5H complex are assayed. Data obtained using different concentrations of GAL-5H are used to calculate values for the number, affinity, and association of GAL-5H with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide sequence encoding a polypeptide comprising the amino acid sequence of SEQ ID NO:1.

2. A hybridization probe comprising of the polynucleotide sequence of claim 1.

3. An isolated and purified polynucleotide sequence consisting of SEQ ID NO:1.

4. A polynucleotide sequence which is fully complementary to the polynucleotide sequence of claim 1.

5. A hybridization probe comprising the polynucleotide sequence of claim 4.

6. An expression vector containing the polynucleotide sequence of claim 1.

7. A host cell containing the expression vector of claim 6.

8. A method for producing a polypeptide comprising the amino acid sequence of SEQ ID NO:1, the method comprising the steps of:
 a) culturing the host cell of claim 7 under conditions suitable for the expression of the polypeptide; and
 b) recovering the polypeptide from the host cell culture.

9. A method for detection of a polynucleotide encoding a polypeptide comprising the amino acid sequence of SEQ ID NO:1 in a biological sample containing nucleic acid material, the method comprising the steps of:

a) hybridizing the polynucleotide of claim 4 to the nucleic acid material of the biological sample, thereby forming a hybridization complex; and
 b) detecting the hybridization complex, wherein the presence of the hybridization complex correlates with the presence of a polynucleotide sequence encoding the polypeptide in the biological sample.

* * * * *

UNITED STATES PATENT AND TRADEMARK OFFICE
CERTIFICATE OF CORRECTION

PATENT NO. : 5,837,493
DATED : Nov. 17, 1998
INVENTOR(S) : Jennifer L. Hillman et al.

It is certified that error appears in the above-identified patent and that said Letters Patent is hereby corrected as shown below:

Col. 39, line 62, delete "of" after "comprising"

Col. 39, line 65, delete "1" and insert --2--.

Signed and Sealed this

Seventh Day of December, 1999

Attest:

Q. TODD DICKINSON

Attesting Officer

Acting Commissioner of Patents and Trademarks

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 145 amino acids
( B ) TYPE: amino acid
( C ) STRANDEDNESS: single
( D ) TOPOLOGY: linear ( x i ) SEQUENCE DESCRIPTION: SEQ ID NO:1:

| Met | Ala | Xaa | Ser | Gly | Ser | Gln | Ala | Pro | Tyr | Leu | Ser | Pro | Xaa | Val | Pro |
|---|---|---|---|---|---|---|---|---|---|---|---|---|---|---|---|
| 1 | | | | 5 | | | | | 10 | | | | | 15 | |
| Phe | Ser | Gly | Thr | Xaa | Gln | Gly | Gly | Leu | Tyr | Pro | Ser | Lys | Ser | Ile | Leu |
| | | | 20 | | | | | 25 | | | | | 30 | | |
| Leu | Ser | Gly | Thr | Val | Leu | Pro | Ser | Ala | Gln | Arg | Phe | His | Ile | Asn | Leu |
| | | | 35 | | | | 40 | | | | | 45 | | | |
| Cys | Ser | Gly | Asn | His | Ile | Gly | Phe | His | Leu | Asn | Pro | Arg | Phe | Asp | Glu |
| | | 50 | | | | 55 | | | | | 60 | | | | |
| Asn | Ala | Val | Val | Arg | Asn | Asn | Gln | Ile | Asp | Asn | Xaa | Trp | Gly | Ser | Glu |
| 65 | | | | | 70 | | | | | 75 | | | | | 80 |
| Glu | Arg | Ser | Leu | Pro | Arg | Lys | Met | Pro | Phe | Val | Arg | Gly | Gln | Ser | Phe |
| | | | | 85 | | | | | 90 | | | | | 95 | |
| Ser | Val | Trp | Ile | Leu | Cys | Glu | Ala | His | Cys | Leu | Lys | Val | Ala | Val | Asp |
| | | | 100 | | | | | 105 | | | | | 110 | | |
| Gly | Gln | His | Leu | Phe | Glu | Tyr | Tyr | His | Arg | Leu | Arg | Asn | Leu | Pro | Thr |
| | | 115 | | | | | 120 | | | | | 125 | | | |
| Ile | Asn | Arg | Leu | Glu | Val | Gly | Gly | Asp | Ile | Gln | Leu | Thr | His | Val | Gln |
| | 130 | | | | | 135 | | | | | 140 | | | | |
| Thr | | | | | | | | | | | | | | | |
| 145 | | | | | | | | | | | | | | | |

( 2 ) INFORMATION FOR SEQ ID NO:2:

( i ) SEQUENCE CHARACTERISTICS:
( A ) LENGTH: 558 base pairs
( B ) TYPE: nucleic acid
( C ) STRANDEDNESS: single
( D ) TOPOLOGY: linear ( x i ) SEQUENCE DESCRIPTION: SEQ ID NO:2:

```
CTCTACAANG  GACTTCCTAG  TGGGTGTGAA  TGGCAGCGGT  GGCCACAGNG  GCGGCGGNGA      60

GATGGCCTTN  AGCGGTTCCC  AGGCTCCCTA  CCTGAGTCCA  NCTGTCCCCT  TTTCTGGGAC     120

TNTTCAAGGA  GGGCTGTACC  CATCCAAGTC  CATCCTCCTG  TCAGGCACTG  TCCTGCCCAG     180

TGCTCAGAGG  TTCCACATCA  ACCTGTGCTC  TGGGAACCAC  ATCGGCTTYC  ACCTGAACCC     240

CCGTTTTGAT  GAGAATGCTG  TGGTCCGCAA  CAACCAGATC  GACAACTYCT  GGGGGTCTGA     300
```

| | | | | | |
|---|---|---|---|---|---|
| GGAGCGAAGT | CTGCCCCGAA | AAATGCCCTT | CGTCCGTGGC | CAGAGCTTCT | CAGTGTGGAT | 360 |
| CTTGTGTGAA | GCTCACTGCC | TCAAGGTGGC | CGTGGATGGT | CAGCACCTGT | TTGAATACTA | 420 |
| CCATCGCCTG | AGGAACCTGC | CCACCATCAA | CAGACTGGAA | GTGGGGGGNG | ACATCCAGCT | 480 |
| GACCCATGTG | CAGACATAGG | CGGCTTCCTG | GGCCTGGGGC | CGGGGGTNGG | GTGTGGGGCA | 540 |
| GTCTTGGTCT | TCATAAAC | | | | | 558 |

( 2 ) INFORMATION FOR SEQ ID NO:3:

( i ) SEQUENCE CHARACTERISTICS:
        ( A ) LENGTH: 149 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

```
Met Phe Ser Thr Xaa Gly Ile Pro Pro Met Met Tyr Pro His Pro Gly
  1               5                  10                  15
Tyr Pro Met Pro Phe Ile Thr Thr Ile Leu Gly Gly Leu Tyr Pro Ser
             20                  25                  30
Lys Ser Ile Leu Leu Ser Gly Thr Val Leu Pro Ser Ala Gln Arg Phe
         35                  40                  45
His Ile Asn Leu Cys Ser Gly Asn His Ile Ala Phe His Leu Asn Pro
     50                  55                  60
Arg Phe Asp Glu Asn Ala Val Val Arg Asn Thr Gln Ile Asp Asn Phe
 65                  70                  75                  80
Trp Gly Ser Glu Glu Arg Ser Leu Pro Arg Lys Met Pro Phe Val Arg
                 85                  90                  95
Gly Gln Ser Phe Ser Val Trp Ile Leu Cys Glu Ala His Cys Leu Lys
             100                 105                 110
Val Ala Val Asp Gly Gln His Leu Phe Glu Tyr Tyr His Arg Leu Arg
         115                 120                 125
Asn Leu Pro Thr Ile Asn Arg Leu Glu Val Gly Gly Asp Ile Gln Leu
     130                 135                 140
Thr His Val Gln Thr
145
```

( 2 ) INFORMATION FOR SEQ ID NO:4:

( i ) SEQUENCE CHARACTERISTICS:
        ( A ) LENGTH: 1167 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

| | | | | | |
|---|---|---|---|---|---|
| GAACGGGATC | CTCTTCGTGC | AGTACTTCCA | CCGCGTGCCC | TTCCACCGTG | TGGACACCAT | 60 |
| CTCCGTCAAT | GGCTCTGTGC | AGCTGCCAAC | CCGGCTCCCA | TTACCCAGAC | AGTCATCCAC | 120 |
| ACAGTGCAGA | GCGCCCCTGG | ACAGATGTTC | TCTACTNCCG | GCATCCACC | TATGATGTAC | 180 |
| CCCCACCCCG | GCTATCCGAT | GCCTTTCATC | ACCACCATTC | TGGGAGGGCT | GTACCCATCC | 240 |
| AAGTCCATCC | TCCTGTCAGG | CACTGTCCTG | CCCAGTGCTC | AGAGGTTCCA | CATCAACCTG | 300 |
| TGCTCTGGGA | ACCACATCGC | CTTCCACCTG | AACCCCGTT | TTGATGAGAA | TGCTGTGGTC | 360 |
| CGCAACACCC | AGATCGACAA | CTTCTGGGGG | TCTGAGGAGC | GAAGTCTGCC | CCGAAAAATG | 420 |
| CCCTTCGTCC | GTGGCCAGAG | CTTCTCAGTG | TGGATCTTGT | GTGAAGCTCA | CTGCCTCAAG | 480 |
| GTGGCCGTGG | ATGGTCAGCA | CCTGTTTGAA | TACTACCATC | GCCTGAGGAA | CCTGCCCACC | 540 |

-continued

| | | | | | |
|---|---|---|---|---|---|
| ATCAACAGAC | TGGAAGTGGG | GGGCGACATC | CAGCTGACCC | ATGTGCAGAC | ATAGGCGGCT | 600
| TCCTGGCCCT | GGGGCCGGGG | GCTGGGGTGT | GGGGCAGTCT | GGGTCCTCTC | ATCATCCCCA | 660
| CTTCCCAGGC | CCAGCCTTTC | CAACCCTGCC | TGGGATCTGG | GCTTTAATGC | AGAGGCCATG | 720
| TCCTTGTCTG | GTCCTGCTTC | TGGCTACAGC | CACCCTGGAA | CGGAGAAGGC | AGCTGACGGG | 780
| GATTGCCTTC | CTCAGCCGCA | GCAGCACCTG | GGGCTCCAGC | TGCTGGAATC | CTACCATCCC | 840
| AGGAGGCAGG | CACAGCCAGG | GAGAGGGGAG | GAGTGGGCAG | TGAAGATGAA | GCCCCATGCT | 900
| CAGTCCCCTC | CCATCCCCCA | CGCAGCTCCA | CCCCAGTCCC | AAGCCACCAG | CTGTCTGCTC | 960
| CTGGTGGGAG | GTGGCCTCCT | CAGCCCCTCC | TCTCTGACCT | TTAACCTCAC | TCTCACCTTG | 1020
| CACCGTGCAC | CAACCCTTCA | CCCCTCCTGG | AAAGCAGGCC | TGATGGCTTC | CCACTGGCCT | 1080
| CCACCACCTG | ACCAGAGTGT | TCTCTTCAGA | GGACTGGCTC | CTTTCCCAGT | GTCCTAAAA | 1140
| TAAAGAAATG | AAAATGCTTG | TTGGCAC | | | | 1167

( 2 ) INFORMATION FOR SEQ ID NO:5:

( i ) SEQUENCE CHARACTERISTICS:
        ( A ) LENGTH: 145 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: GenBank
        ( B ) CLONE: 727176

( x i ) SEQUENCE DESCRIPTION: SEQ ID NO:5:

```
Met Ser Ser Phe Ser Thr Gln Thr Pro Tyr Pro Asn Leu Ala Val Pro
 1           5                  10                 15
Phe Phe Thr Ser Ile Pro Asn Gly Leu Tyr Pro Ser Lys Ser Ile Val
             20              25              30
Ile Ser Gly Val Val Leu Ser Asp Ala Lys Arg Phe Gln Ile Asn Leu
         35              40              45
Arg Cys Gly Gly Asp Ile Ala Phe His Leu Asn Pro Arg Phe Asp Glu
     50              55              60
Asn Ala Val Val Arg Asn Thr Gln Ile Asn Asn Ser Trp Gly Pro Glu
 65              70              75              80
Glu Arg Ser Leu Pro Gly Ser Met Pro Phe Ser Arg Gly Gln Arg Phe
             85              90              95
Ser Val Trp Ile Leu Cys Glu Gly His Cys Phe Lys Val Ala Val Asp
             100             105             110
Gly Gln His Ile Cys Glu Tyr Ser His Arg Leu Met Asn Leu Pro Asp
             115             120             125
Ile Asn Thr Leu Glu Val Ala Gly Asp Ile Gln Leu Thr His Val Glu
     130             135             140
Thr
145
```